United States Patent [19]

Omura et al.

[11] Patent Number: 4,666,715
[45] Date of Patent: May 19, 1987

[54] ANTIBIOTIC AM-5344-A$_2$ SUBSTANCE AND PROCESS FOR THE PRODUCTION THEREOF

[75] Inventors: Satoshi Omura, Tokyo; Yuzuru Iwai, Chiba; Kiyoizumi Hinotozawa, Kanagawa; Atsushi Hirano, Miyazaki, all of Japan

[73] Assignee: Kitasato Institute, Tokyo, Japan

[21] Appl. No.: 507,385

[22] Filed: Jun. 24, 1983

Related U.S. Application Data

[63] Continuation-in-part of Ser. No. 329,463, Dec. 10, 1981, abandoned.

[30] Foreign Application Priority Data

Dec. 17, 1980 [JP] Japan ................................ 55-177107

[51] Int. Cl.$^4$ ......................... A61K 35/74; C12P 1/06

[52] U.S. Cl. ..................................... 424/122; 435/169
[58] Field of Search ......................... 424/122; 435/169

[56] References Cited

PUBLICATIONS

Chemical Abstracts, 97:180143h (1982).

*Primary Examiner*—Jerome D. Goldberg

[57] ABSTRACT

An antibiotic AM-5344-A$_2$ substance, and a process for the preparation of the antibiotic AM-5344-A$_2$ substance are described. The antibiotic AM-5344-A$_2$ substance is prepared by cultivating an AM-5344-A$_2$ substance-producing strain belonging to the genus Streptomyces, for example, Streptomyces sp. Am-5344 in a nutrient medium, and recovering the Am-5344-A$_2$ substance from the culture.

3 Claims, 2 Drawing Figures

ANTIBIOTIC AM-5344-A$_2$ SUBSTANCE AND PROCESS FOR THE PRODUCTION THEREOF

This application is a continuation-in-part of Ser. No. 329,463, filed Dec. 10, 1981, now abandoned.

FIELD OF THE INVENTION

The present invention relates to a novel antibiotic AM-5344-A$_2$ substance and a process for the production thereof.

BACKGROUND OF THE INVENTION

It has been known that various microbial species, e.g., of the genus Streptomyces, may produce antibiotics upon cultivation in a nutrient medium containing assimilable carbon and nitrogen sources. However, a continuing need exists for new and useful antibiotic substances.

SUMMARY OF THE INVENTION

According to the invention, it has now been found that a microorganism strain AM-5344 isolated from soil collected in Chiba, Japan, is capable of producing a novel antibiotic substance herein designated as antibiotic AM-5344-A$_2$ substance. This antibiotic AM-5344-A$_2$ substance is believed to be a novel substance in view of the physical and chemical properties thereof.

The present invention, therefore, provides: (1) an antibiotic AM-5344-A$_2$ substance having physical and chemical properties as described hereinafter; and (2) a process for producing the antibiotic AM-5344-A$_2$ substance by cultivating an antibiotic AM-5344-A$_2$-producing strain belonging to the genus Streptomyces in a nutrient medium under aerobic conditions to accumulate the antibiotic AM-5344-A$_2$ substance therein and isolating the antibiotic AM-5344-A$_2$ substance therefrom.

DETAILED DESCRIPTION OF THE INVENTION

The physical and chemical properties of the antibiotic AM-5344-A$_2$ substance of the invention are as follows:

(1) Elemental Analysis: C- 63.87% H: 3.96% N: 2.29%

(2) Molecular Weight: Mass spectral analysis (FD mass spectrum) shows that there are a signficant peak at a mass number of 527 and other peaks at 528 and 529.

(3) Melting Point: More than 290° C.

(4) Specific Rotatory Power: $[\alpha]_D^{20} = -214°$ (C=0.25, chloroform)

Figure 1:
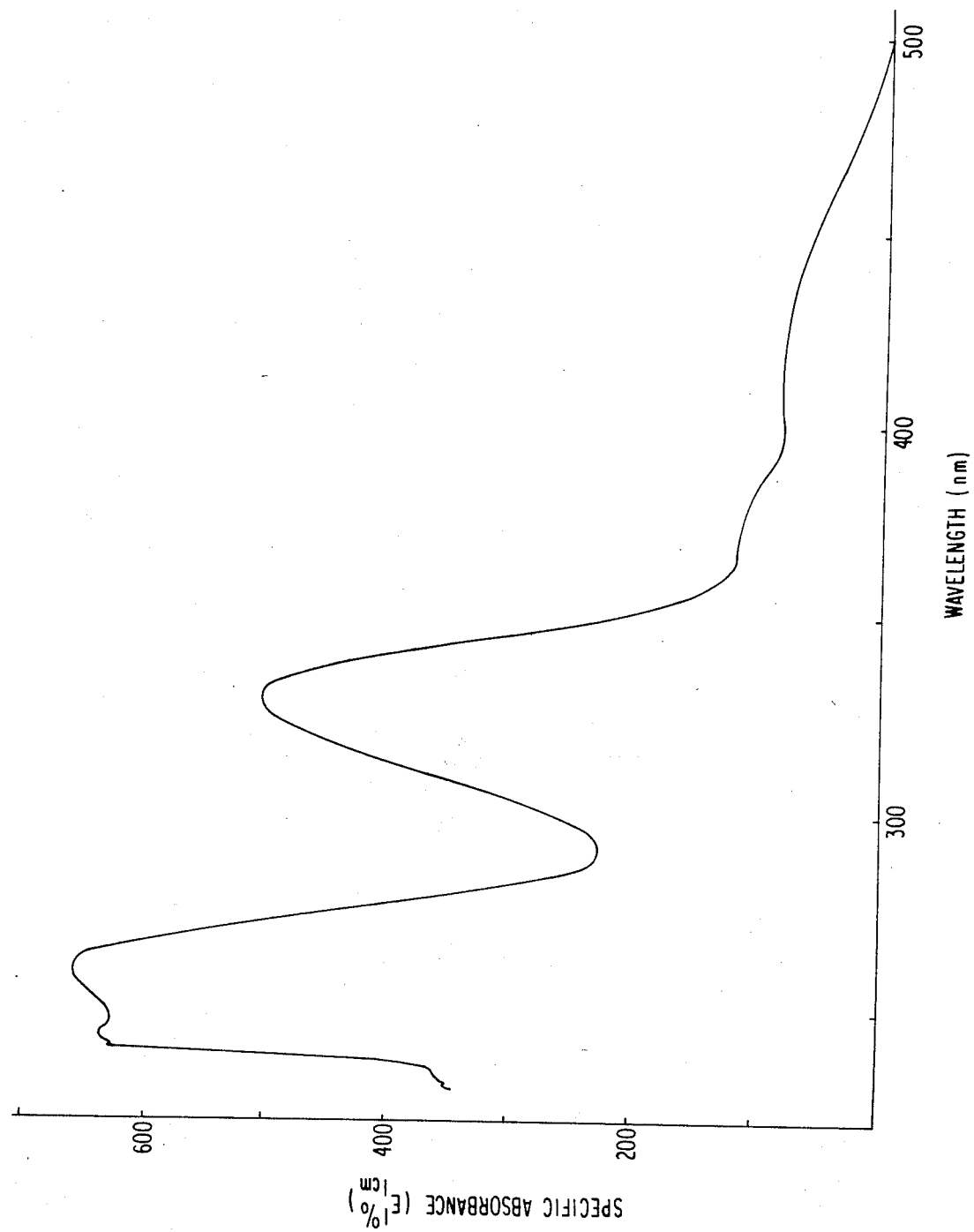
FIG. 1 is an ultraviolet absorption spectrum of the antibiotic AM-5344-A$_2$ substance (as measured in chloroform)

(5) Ultraviolet Absorption Spectrum: Shown in FIG. 1. The absorption maximums ($E_{1cm}^{1\%}$) in chloroform are 260 nm (668), 329 nm (514), 375 nm shoulder (117), and 420 nm shoulder (86).

Figure 2:
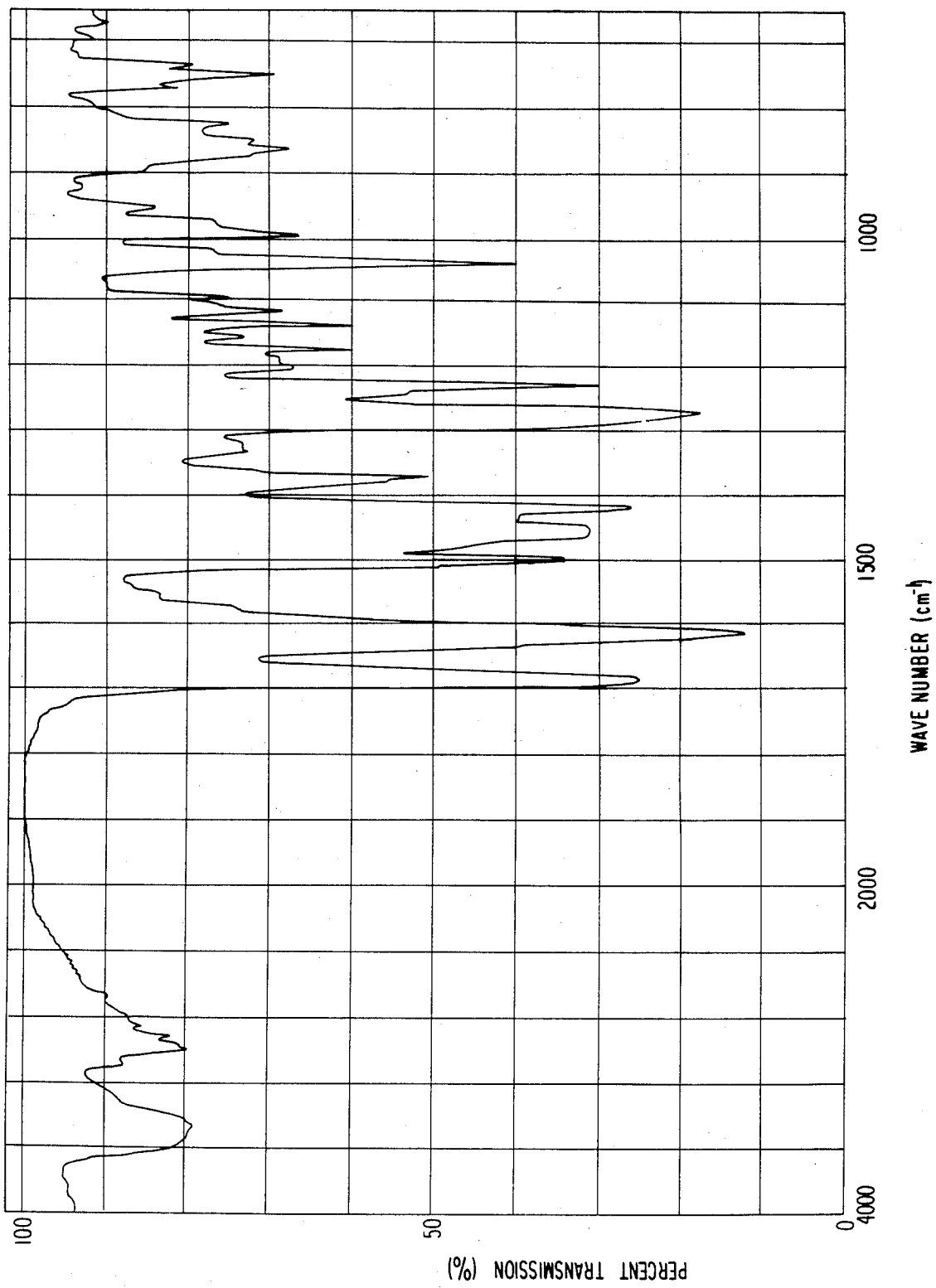
FIG. 2 is an infrared absorption spectrum of the antibiotic AM-5344-A$_2$ substance (as measured in a potassium bromide tablet).

(6) Infrared Absorption Spectrum: Shown in FIG. 2 (as determined by the potassium bromide tablet method).

(7) Solubility: Soluble in chloroform; sparingly soluble in organic solvents, such as acetone, ethyl acetate, and benzene, and lower alcohols; and insoluble in n-hexane, ethyl ether, and water.

(8) Color Reactions: Positive to the ferric chloride reaction and Rydon Smith reaction; and negative to the Dragendorff reaction and ninhydrin reaction.

(9) Property (acidity): Neutral

(10) Color: Orange

(11) Rf Values: Rf Values as determined by conventional silica gel thin layer chromatography (TLC aluminum sheet, silica gel 60F$_{254}$, produced by Merck and Co.; thickness: 0.2 mm) are as follows:

|  |  | Rf |
| --- | --- | --- |
| (a) | Chloroform/methanol (40/1) | 0.32 |
| (b) | Benzene/acetone (1/1) | 0.68 |
| (c) | Benzene/methanol (4/1) | 0.58 |
| (d) | Ethyl acetate | 0.20 |
| (e) | n-Butanol/acetic acid/water (4/1/1) | 0.61 |

The biological characteristics of the antibiotic AM-5344-A$_2$ substance of the invention are as follows: (1) Antibacterial Activities The minimum inhibitory concentration (M.I.C.) as determined by the agar dilution method (standardized by Nippon Kagaku Ryoho Gakka) is shown in Table 1 below.

TABLE 1

| Test Organism | MIC (mcg/ml) |
| --- | --- |
| Staphylococcus aureus TPR 23 | 0.05 |
| Streptococcus faecalis ATCC 8043 | 0.20 |
| Micrococcus flavus IFO 3242 | 0.20 |
| Sarcina lutea ATCC 9341 | 3.13 |
| Bacillus subtilis ATCC 6633 | 0.10 |
| Bacillus cereus IFO 3466 | >100 |
| Escherichia coli NIHJ Jc-2 | >100 |
| Salmonella typhimurium | >100 |
| Klebsiella pneumoniae IFO 3512 | >100 |
| Enterobacter aerogenes IFO 5467 | >100 |
| Proteus vulgaris A 33 | >100 |
| Pseudomonas aeruginosa IAM 1054 | >100 |
| Clostridium perfringens ATCC 13124 | 0.006 |
| Eubacterium lentum ATCC 25559 | 0.006 |
| Bifidobacterium bifidum ATCC 11146 | 0.098 |
| Peptococcus prevotii ATCC 9321 | 0.098 |
| Lactobacillus acidophilus IFO 3205 | 0.049 |
| Bacteroides fragilis ATCC 23745 | 0.049 |

(2) Antitrichomonas Activity:

The minimum inhibitory concentraion as determined by the liquid medium dilution method is shown below. As the liquid medium, Trichosel broth (produced by Beckton, Dickinson and Company) was used.

|  | MIC (mcg/ml) |
| --- | --- |
| Trichomonas foetus | 0.05 |

(3) Toxicity

The LD$_{50}$ of the antibiotic AM-5344-A$_2$ substance in mice was 50 mg/kg by intraperitoneal administration and more than 150 mg/kg by oral adminitration.

As can be seen from the above described results, the antibiotic AM-5344-A$_2$ substance of the invention exhibits antibacterial and antiprotozoal activities against Gram-positive and anaerobic bacterium, and trichomonas. Thus the antibiotic AM-5344-A$_2$ substance of the invention can be used as an antimicrobial agent, and in particular, it is useful for prevention and treatment of anerobic bacteria infectious diseases. In view of its antibacterial spectrum, the substance may also be used as an animal medicine.

The following example illustrates the use of the AM-5344-A$_2$ substance against bacterial infection in vivo.

EXAMPLE A

Chemotherapeutic Effect on Experimental Mice Subcutaneous Abscess due to *Bacteroides fragilis*:

As an infective bacteria, *Bacteroides fragilis* 5550 was used. MIC of the AM-5344-A$_2$ substance against this bacteria was 0.05 μg/ml.

ddy Male mice each weighing about 20 g were used, 5 mice per group.

*Bacteroides fragilis* was cultured at 37° C. in a GAM plate culture medium (manufactured by Nissui Pharmaceutical Co., Ltd.) in an anaerobic jar and the bacteria was used at a concentration of $10^8$ cells/ml. 0.3 ml of the bacteria was inoculated subcutaneously at the abdominal wall of each test mouse to form an abscess at the inoculated site.

Dosages of the AM-5344-A$_2$ substance were 5, 2.5 and 1.25 mg/kg/day (test groups 1, 2 and 3, respectively). The AM-5344-A$_2$ substance was subcutaneously injected once a day for seven consecutive days from the 4th Day after the inoculation of *Bacteroides fragilis*. The anti-bacterial effect was determined by the "ratio of abscess" (number of mice having an abscess/number of mice in the group) at the inoculated site on the 10th Day. The group to which this substance was not administered was the control group. The results are shown in Table A.

TABLE A

| Drug | Dose in Test Group (mg/kg/day) | Ratio of Abscess |
| --- | --- | --- |
| AM-5344-A$_2$ | 1.25 | 4/5 |
|  | 2.5 | 2/5 |
|  | 5.0 | 1/5 |
| Control | 0 | 5/5 |

As is evident from the test results shown in Table A, the substance of this invention, AM-5344-A$_2$, shows an excellent chemotherapeutic effect against anaerobic bacterial infection.

In the case of administering the antibiotic AM-5344-A$_2$ as a chemotherapeutic agent against anaerobic bacterial infections, the intraperitoneal administration experimentally shown is an example but other methods such as as oral administration, intravenous injection, subcutaneous injection, intra-rectal administration using a suppository, and the like are also applicable. In the case that the antibiotic AM-5344-A$_2$ is employed as a chemotherapeutic agent against anaerobic bacterial infections, suitable medical preparations are adopted depending upon the route for administration described above.

As injections, preparations such as suspensions, solutions or powders which are dissolved upon use, etc. can be employed.

For oral administration, tablets, pills or capsules obtained by adding carriers or vehicles, e.g., CaCO$_3$, lactose, sucrose, gelatin, cyclodextrin, etc., are employed. Further, enteric coated tablets, etc., utilizing these preparations can be employed.

As suppositories, those prepared using bases such as cacao butter, laurin butter, polyethylene glycol or a mixture thereof can be employed.

In the case of using this antibiotic AM-5344-A$_2$ as a chemotherapeutic agent against a anaerobic bacterial infections, dosage and administration schedule are suitable chosen taking the patients and their conditions, etc. into account.The dosage and schedule also vary depending upon route for administration and medical preparation employed; however, it is generally desired that the dosage at one time be in the range of 0.05 to 10 mg/kg body weight and the number of times of administration per day be once to 6 (at appropriate intervals) times per day, depending upon improvement of condition.

EXAMPLE B

Anti-Cancer Effects of AM-5344-A$_2$

The antibiotic, AM-5344-A$_2$ substance, exhibited an obvious prevention effect against Ehrlich-Lettre ascites and lymphoma P-388 transplanted in mice in the following tests.

The methods for anti-cancer testing using the AM-5344-A$_2$ substance and the test results are shown below.

ddy Mice (each weighting about 25 g) were divided into 4 groups, each group consisting of 3 mice. Ehrlich carcinoma was intraperitoneally inoculated at a level of $1 \times 10^7$ cells/mouse into each mouse. Two days after the inoculations, the AM-5344-A$_2$ substance was intraperitoneally administered once a day for 4 consecutive days at the dose of 1.25 mg/kg/day for the first group, at the dose of 2.5 mg/kg/day for the second group and, at the dose of 5.0 mg/kg/day for the third group; the fourth group to which this substance was not administered was the control group.

The mice were fed for 32 days after the inoculation and the prevention effect of the AM-5344-A$_2$ substance against Ehrlich-Lettre ascites as determined by mean survival days in the respective groups. The results are shown in Table B.

TABLE B

| Group | Dose (mg/kg/day) | Survival Days*** | MSD (days)* | T/C (%) |
| --- | --- | --- | --- | --- |
| 1 | 1.25 | 27, 32, S** | 32 | 145 |
| 2 | 2.5 | 32, 32, S | 32 | 145 |
| 3 | 5.0 | 7, 29, S | 29 | 132 |
| 4 | — | 22, 22, 28 | 22 | 100 |

*mean survival days
**survival
***of each mouse

Next, the method for anti-cancer testing of the AM-5344-A$_2$ substance against mouse lymphoma P-388 and the rest results are shown below.

CDF$_1$ mice (each weighing about 25 g) were divided into 5 groups, the first four groups each consisting of 2 mice each. P-388 was intraperitoneally inoculated at a level of $1 \times 10^5$ cells/mouse into each mouse. On th 2nd, 3rd, 4th, 5th, 8th, 9th, 10th, 11th and 12th Days after the inoculation, the AM–5344-A$_2$ substance was intraperitoneally administered once a day at the dose of 0.625 mg/kg/day for the first group, at the dose of 1.25 mg/kg/day for the second group, at the dose of 2.5 mg/kg/day for the third group and at 5.0 mg/kg/day for the fourth group. The fifth group consisted of 5 mice to which the AM-5344-A$_2$ substance was not administered and was the control group.

The mice were fed for 16 days after the inoculation and the prevention effect of the AM-5344-A$_2$ substance against P-388 was determined by mean survival days of the respective groups. The results are shown in Table C.

TABLE C

| Group | Dose (mg/kg/day) | Survival Days** | MSD (days)* | T/C (%) |
|---|---|---|---|---|
| 1 | 0.625 | 13, 14 | 13.5 | 117 |
| 2 | 1.25 | 14, 15 | 14.5 | 126 |
| 3 | 2.5 | 14, 16 | 15 | 130 |
| 4 | 5.0 | 6, 8 | 7 | 61 |
| 5 | — | 11, 11, 12, 11, 12 | 11.4 | 100 |

*mean survival days
**of each mouse

As is evident from the test results shown in Tables B and C, the compound of the present invention, AM-5344-A$_2$ shows an excellent anti-cancer effect on trasnsplanted tumors.

In the case of using the antibiotic AM-5344-A$_2$ as an anti-cancer agent for transplanted tumors, the intraperitoneal administration experimentally shown is an example but other methods such as oral administration, intravenou injection, subcutaneous injection, intra-rectal administration using a suppository, and the like are also applicable. In the case that this antibiotic AM-5344-A$_2$ is employed as an anti-cancer agent for transplanted tumors, suitable medical preparations are adopted depending upon route for administration described above.

As injection, preparations such as suspensions, solutions or powders which are dissolved upon use, etc. can be employed.

For oral administration, tablets, pills or capsules obtained by adding carriers or vehicles, e.g., CaCO$_3$, lactose, sucrose, gelatin, cyclodextrin, etc., can be employed. Further, enteric coated tablets, etc., utilizing these preparations can be employed.

As suppositories, those prepared using bases such as cacao butter, laurin butter, polyethylene glycol or a mixture thereof can be employed.

In the case of using the antibiotic AM-5344-A$_2$ as an agent, dosage and administration schedule are suitably chosen taking the patients and their conditions, etc. into account. The dosage and schedule also vary depending upon route for administration and the medical preparation used; however, it is generally desired that the dosage at one time be in the range of 0.05 to 10 mg/kg body weight and the number of times of administration per day be once to 6 at (appropriate intervals) times per day, depending upon improvement of condition.

It is contemplated that the AM-5344-A$_2$ substance can be employed as a chemotherapeutic agent and to treat bacterial infection.

As a result of a comparative study on the physical and chemical, and biological characteristics of the antibiotic AM-5344-A$_2$ substance with reference to those of the known antibiotics, it has been determined that the antibiotic AM-5344-A$_2$ substance is a novel substance.

Examples of antibiotics which are neutral, fat-soluble, provides an ultraviolet absorption spectrum having the absorption maximums near 260 nm, 329 nm, 375 nm shoulder, and 420 nm shoulder, and are effective to Gram-positive bacterius include Chartreusin (Giorn. Microbiol., 1, 176 (1955)), Cerulomycin (Antibiotiki, Moscow, 2, 16 to 20 (1957)), Mekemycin (Meiji Yakkadaigaku Kenkyu Kiyo, 2, 1 to 8 (1963)), and Thermorubin A (Clin. Med., 71, 511 to 521 (1964)). The antibiotic AM-5344-A$_2$ substance is clearly different from Chartreusin in that the former contains nitrogen, whereas the latter contains no nitrogen. Merulomycin is a polyene antibiotic in the form of colorless crystal (whereas the color of the antibiotic AM-5344-A$_2$ substance is orange), and the specific absorbance at each maximum absorption of the ultraviolet absorption spectrum differs significantly from that of the antibiotic AM-5344-A$_2$ substance. Also, the antibiotic AM-5344-A$_2$ substance is different from Mekemycin and Thermorubin in that the former contains nitrogen, wherein the latter contain no nitrogen. As described above, the antibiotic AM-5344-A$_2$ substance is clearly distinguishable over such known antibiotics.

A typical example of microorganisms which are used for the production of the antibiotic AM-5344-A$_2$ substance of the invention is Streptomyces sp. AM-5344 which was newly isolated from a soil sample collected in Saiwai-cho, Chiba-shi, Chiba, Japan.

The characteristics of the AM-5344 strain are as follows:

(1) Morphological Characteristics

The vegetative hypha grows abundantly on both natural and synthetic culture media, and, usually, it has no septal wall. The aerial mycelium grows moderately in glycerol-asparagine agar, tyrosine agar, etc., but grows scantily or not at all in other culture media. The tone of the aerial mycelium is yellow to grey, and it is in the form of powder or velvet.

Microscopic observation shows that the sporophore is in straight or loop form, there is no growth of spores in glycerol-asparagine agar and tyrosine agar, and that a chain of 10 to 50 spores is formed in starch-inorganic salt agar. The surface of spores is smooth. Sclerotia, sporangium, and zoospores are not observed.

(2) Culture Characteristics

The culture characteristics of the AM-5344 strain were observed on various known culture media according to the method devised by E. B. Shirling (Int. J. Syst. Bacteriol, Vol. 16, page 313 (1966)). The results are shown in Table 2. The color is identified according to the color standard of the *Color Harmony Manual*, 4th Ed. (published by Container Corporation of America, Chicago (1958)), and it is shown in Table 2 along with the code number in parenthesis. Observation was performed at the end of cultivation at 27° C. for 2 weeks unless other wise indicated.

TABLE 2

| Culture Medium | Growth | Reverse Color | Aerial Mycerium | Soluble Pigment |
|---|---|---|---|---|
| Glucose-Nitrate Agar | Fair growth, elevated Bright gold (2 pc) | Bright gold (2 pc) | None | Bright gold (2 pc) |
| Sucrose-Nitrate Agar | Fair growth, permiated Bamboo (2 gc) to mustard tan (2 lg) | Bamboo (2 gc) to mustard brown (2 ni) | Thin growth in velvet form Cobalt tan (2 ge) | Cream (1½ ca) |
| Glycerol-Calcium Malate Agar | Fair growth, diffused Pearl (3 ba) to bamboo (2 gc) | Light ivory (2 ca) to bamboo (2 gc) | Poor growth in powder form Natural (2 dc) | Not produced |
| Glucose-Asparagine Agar | Fair growth Light antique gold (1½ ic) | Light antique gold (1½ ic) | None | Light yellow (1½ ea) |
| Glycerol-Agaparagine | Fair growth, permeated | Antique gold | Medium growth in | Not produced |

TABLE 2-continued

| Culture Medium | Growth | Reverse Color | Aerial Mycerium | Soluble Pigment |
|---|---|---|---|---|
| Agar (ISP) | Antique gold (1½ ne) | (1½ ne) | velvet form White (a) | |
| Starch-Inorganic Salt Agar (ISP) | Fair growth, permeated Center area: Mustard gold (2 ne) Circumferential area: Mustard brown (2 pl) | Dull gold (2 ng) | Poor growth in powder form Light ivory (2 ca) | Not produced |
| Tyrosine Agar (ISP) | Fair growth, elevated Bisquit ecru (2 ec) | Citron (1 gc) | Medium growth in velvet form Dark cobalt grey (2 ih) | Not produced |
| Yeast-Malt Agar | Fair growth, permeated and elevated Honey gold (2 ic) | Honey gold (2 ic) | Very poor growth White (a) | Not produced |
| Oatmeal Agar (ISP) | Fair growth, permeated Mustard brown (2 pi) | Mustard brown (2 pi) | Very poor growth White (a) | Not produced |
| Peptone-Yeast Iron Agar | Fair growth, elevated Cream (1½ ca) | Light wheat (2 ea) | None | Not produced |
| Glucose-Peptone Agar | Fair growth, permeated and elevated Sunlight yellow (1½ ia) | Sunlight yellow (1½ ia) | None | Butter yellow (1½ ga) |
| Nutrient Agar | Medium growth, permeated and elevated Light wheat (2 ea) | Light wheat (2 ea) | None | Not produced |

Note: ISP
Medium selected by International Streptomyces Project.

(3) Physiological Characteristics
(a) Production of Melanine Pigment
  (1) Tyrosine Agar Negative
  (2) Peptone-Yeast Iron Agar: Negative
  (3) Glucose-Peptone-Gelatine Medium: Negative Stab (21° to 23° C.)
  (4) Tryptone-Yeast Liquid: Negative
(b) Tyrosinase Reaction: Negative
(c) Production of Hydrogen Sulfide: Negative
(d) Reduction of Nitrates: Negative
(e) Liquefaction of Gelatin (21° to 23° C.); Negative (glucose-peptone-gelatin medium)
(f) Hydrolysis of Starch: Positive
(g) Coagulation of Skim Milk (36° C.): Negative
(h) Peptonization of Skim Milk (36° C.): Positive
(i) Decomposition of Cellulose: Negative
(j) Growth Temperature Range: 6° to 36° C.
(k) Utilization of Carbon Sources
  (1) Well utilizable: D-Glucose, D-Mannitol, D-Fructose, L-Arabinose, i-Inositol, Rhamnose, Raffinose, Maltose
  (2) Slightly utilizable: D-xylose
  (3) Not utilizable: Sucrose
(4) Cell Wall Composition
Diaminopimelic acid is of LL-isomer, and arabinose and galactose are not observed.

The above described characteristics of the AM-5344 strain as used herein can be summarized as follows:

(1) the cell wall composition contains LL-diaminopimelic acid; (2) the strain has the morphological characteristics that straight or loop-like sporophore are formed, and spores have a smooth surface; (3) the strain has the culture characteristics that the vegetative hypha is yellow to dark brown, which color does no change at different pHs, and the aerial mycelium is yellow to grey; and (4) the strain produces yellow soluble pigments in sucrose nitrate agar, glucose asparagino agar, etc., but does not produce melanine pigment.

From these results it was concluded that the AM-5344 strain belongs to the genus Streptomyces, and according to the Pridham and Strainer classification ( see *Bergey's Manual of Determinative Bacteriology*, 8th Ed., pages 748 to 829 (1974)), belongs to the yellow or grey series.

The AM-5344 strain has been named "Streptomyces sp. AM-5344" and deposited in the international depository, Fermentation Research Institute, Agency of Industrial Science and Technology, Ministry of International Trade and Industry of Japan under FERM BP-67 deposited May 1, 1981, which was transferred from FIERM-P 5722 deposited Sept. 29, 1980.

Similar to other strains of the genus Streptomyces, the AM-5344 strain can be modified easily in its properties. Variation can be caused artificially by irradiation with, for example, ultraviolet rays, X-rays, radioactive rays, and chemicals. Thus, in addition to such variants, microorganisms belonging to the genus Streptomyces, can be used in the invention provided that they have the ability to produce the antibiotic AM-5344-$A_2$ substance.

The antibiotic AM-5344-$A_2$ substance-producing microorganisms, can be cultivated in a medium containing carbon sources, nitrogen sources, inorganic compounds, and the like which is usually used for the cultivation of known microorganisms. Carbon sources may be assimilable carbohydrates, and examples of carbon sources which can be used include glucose, maltose, lactose, sucrose, starch, dextrin, glycerin, and molasses. Nitrogen sources may be assimilable nitrogen compounds, and examples of nitrogen sources which can be used include soybean meal, corn steep liquor, cotton seed soil, peptone, meat extract, yeast extract, dry yeast, casein hydrolyzates, ammonium salts, and nitrates. In addition, if necessary, inorganic salts such as phosphates, and magnesium, potassium, calcium, sodium, iron, manganese, and like metal salts can be used.

The cultivation is usually carried out under aerated conditions, and aerated stirring cultivation is suitable. The cultivation temperature can be varied appropriately within a range that permits the growth of microorganisms and the production of the antibiotic AM-5344-$A_2$ substance. Preferably, the cultivation temperature is within the range of 25° to 30° C. The preferred pH is from 6 to 7. Although the cultivation period varies depending on other cultivation conditions, it is usually about 50 to 100 hours, and the cultivation is stopped at an appropriate point at which the concentration of the antibiotic AM-5344-A$_2$ substance reaches a maximum.

The thus-prepared antibiotic AM-5344-A$_2$ substance is isolated from the fermentation broth and purified by conventional isolation and purification techniques.

A typical example of isolation and purification of the antibiotic AM-5344-A$_2$ substance is as follows:

The fermentation broth is first separated into microbial cells and a filtrate. The antibiotic AM-5344-A$_2$ substance contained in the microbial cells is extracted with acetone, ethyl acetate, or the like, or alternatively, after a treatment using methanol, is extracted with an organic solvent such as ethyl acetate and chloroform. On the other hand, the antibiotic AM-5344-A$_2$ substance contained in the filtrate is extracted with ethyl acetate, benzene or the like which is separable from water and capable of dissolving the antibiotic AM-5344-A$_2$ substance. Thereafter, the antibiotic AM-5344-A$_2$ substance is recovered by known techniques which are conventionally used in the purification of fat-soluble substances. For example, an extract (ethyl acetate layer) is concentrated under reduced pressure, and precipitates formed are separated and washed with n-hexane. Thereafter, by silica gel column chromatography using a mixed solvent of chloroform and methanol as an eluent, the antibiotic AM-5344-A$_2$ substance is isolated.

Detection and determination of the antibiotic AM-5344-A$_2$ substance can be performed by a silica gel thin layer chromatography (silica gel 60F$_{254}$ produced by Merck & Co.; thickness: 0.2 mm; eluent: chloroform/methanol=40/1; Rf value of the antibiotic AM-5344-A$_2$ substance: 0.32) and a biological assay method using *Acholeplasma laidlawii* PG-8.

The following examples are given to illustrate the invention in greater detail, although the invention is not limited thereto.

EXAMPLE 1

A seed medium described below was inoculated with one platinum-loop full of a plant culture of Streptomyces sp. AM-5344 strain (FERM BP-67) and cultivated at 27° C. for 2 days. Then, 30 l (liters) of a medium described below was placed in a 50-liter jar fermentor was inoculated with the seed culture in an amount of 1 wt %, and cultivation was performed at 27° C. for 89 hours with aeration and stirring. The seed medium and the medium as used above comprised, respectively, 1.0% glucose, 2.0% starch, 0.5% peptone, 0.5% yeast extract, and 0.4% calcium carbonate, and 2.0% glycerin, 2.0% soybean meal, and 0.3% salt, and they were used after adjustment to pH 7.0 followed by sterilization at 121° C. for 15 minutes.

Then, 30 l of the fermentation broth was subjected to centrifugal separation, and 10 l of ethyl acetate was added to the resulting filtrate. The mixture was fully stirred and then, was subjected to centrifugal separation to separate an ethyl acetate layer. The ethyl acetate extract was concentrated to 500 ml under reduced pressure, and 300 ml of n-hexane was added thereto to remove oily substances. Thus, 3.0 g of brown powder was obtained.

The brown powder was charged into a silica gel column (packed with 120 g of Kiezel Gel 60 produced by Merck & Co.), developed with 1.5 l of chloroform, and then, eluted with 5.0 l of a mixed solvent of chloroform and methanol (50/1) to obtain active fractions (fraction Nos. 130 to 550, 12 ml/cube). These active fractions were concentrated to dryness to obtain 500 mg of brown powder.

The thus obtained brown powder was purified by preparative thin layer chromatography (Rf value: 0.32) using a mixed solvent of chloroform and methanol (40/1), to obtain 150 mg of orange powder of the antibiotic AM-5344-A$_2$ substance. The physical and chemical characteristics of the antibiotic AM-5344-A$_2$ substance were the same as described hereinbefore.

EXAMPLE 2

Thirty liters of a fermentation broth prepared in the same manner as in Example 1 was subjected to centrifugal separation to obtain cells. To these cells was added 10 l of methanol. The mixture was fully stirred, and then was subjected to centrifugal separation to remove the methanol. Then, 5 l of chloroform was added to the cells and stirred to extract active ingredients contained in the cells. The mixture was filtered, and the chloroform layer obtained was concentrated to dryness under reduced pressure to obtain 6 g of a syrup-like material.

The syrup-like material was charged into a silica gel column (packed with 240 g in chloroform; Wako Gel C-200 produced by Wako Chemical Industries Ltd.), developed with chloroform, and eluted with 10 l of a mixed solvent of chloroform and methanol (50/1) to obtain active fractions (fraction Nos. 120 to 500; 25 ml/cube). These active fractions were pooled and concentrated to 700 ml under reduced pressure, and then n-hexane was added thereto. The precipitate formed was separated by filtration, and dried to obtain 1.5 g of orange powder of the antibiotic AM-5344-A$_2$ substance. The physical and chemical characteristics of the antibiotic AM-5344-A$_2$ substance were in agreement with those described hereinbefore.

While the invention has been described in detail and with reference to specific embodiments thereof, it will be apparent to one skilled in the art that various changes and modifications can be made therein without departing from the spirit and scope thereof.

What is claimed is:

1. An antibiotic AM-5344-A$_2$ substance having the following physical and chemical properties:
    (1) Elemental Analysis (by weight): C: 63.87%; H: 3.96%; N: 2.29%;
    (2) Specific Rotary Power: $[\alpha]_D^{20} = -214°$ (C=0.25, chloroform)
    (3) Melting point: more than 290° C.;
    (4) Ultraviolet Absorption Spectrum: Shown in FIG. 1;
    (5) infrared Absorption Spectrum: Shown in FIG. 2;
    (6) Rf Values on Silica Gel Thin Layer Chromatography (TLC aluminum sheet and silica gel 60F$_{254}$ produced by Merck & Co.; thickness: 0.2 mm): 0.32 in chloroform/methanol (40/1); 0.68 in benzene/acetone (1/1); 0.58 in benzene/methanol (4/1); 0.20 in ethyl acetate; and 0.61 in n-butanol/acetic acid/water (4/1/1);
    (7) Solubility: Soluble in chloroform; sparingly soluble in acetone, ethyl acetate; and benzene, and lower alcohols; and insoluble in n-hexane, ethyl ether, and water.

2. A process for preparing an antibiotic AM-5344-A$_2$ substance as defined in claim 1, comprising cultivating as an antibiotic AM-5344-A$_2$ substance-producing strain, Streptomyces sp. AM-5344 having FERM designation FERM BP-67, in a nutrient medium under aerobic stirring conditions at a temperature of 25° to 30° C. and at a pH of 6 to 7 for about 50 to 100 hours, and recovering the antibiotic AM-5344-A$_2$ substance from the culture.

3. A process as in claim 2 wherein the antibiotic AM-5344-A$_2$ substance is recovered from the culture by extracting with acetone, ethyl acetate, chloroform or benzene and isolating by column chromatography.

* * * * *